United States Patent
Kurth

(10) Patent No.: US 7,479,162 B2
(45) Date of Patent: Jan. 20, 2009

(54) LINER

(75) Inventor: Christoph Kurth, Bayreuth (DE)

(73) Assignee: Medi Bayreuth Weihermuller & Voigtmann GmbH & Co., KG., Bayreuth (DE)

( * ) Notice: Subject to any disclaimer, the term of this patent is extended or adjusted under 35 U.S.C. 154(b) by 0 days.

(21) Appl. No.: 10/516,872

(22) PCT Filed: Jun. 4, 2003

(86) PCT No.: PCT/DE03/01835

§ 371 (c)(1),
(2), (4) Date: Nov. 7, 2005

(87) PCT Pub. No.: WO03/101351

PCT Pub. Date: Dec. 11, 2003

(65) Prior Publication Data

US 2006/0089725 A1    Apr. 27, 2006

(30) Foreign Application Priority Data

Jun. 4, 2002    (DE) ................ 202 08 592

(51) Int. Cl.
*A61F 2/80* (2006.01)
(52) U.S. Cl. .......................... 623/36; 623/33
(58) Field of Classification Search ........... 623/33–37
See application file for complete search history.

(56) References Cited

U.S. PATENT DOCUMENTS

| 4,653,473 A | 3/1987 | Kempe |
| 4,664,118 A | 5/1987 | Batters |
| 5,534,034 A * | 7/1996 | Caspers ................ 623/32 |
| 6,014,585 A | 1/2000 | Stoddard |
| 6,861,570 B1 * | 3/2005 | Flick ................ 602/41 |

FOREIGN PATENT DOCUMENTS

| DE | DT2329929 | * | 2/1975 |
| WO | WO 88/00032 | * | 1/1988 |

OTHER PUBLICATIONS

PCT/SE87/00299, WO 88/00032 to Klasson and Kristinsson, Entitled A Sleeve-Shaped Article, Particularly for Amputation Stumps (Including Search Report), 15 pages.
PCT/US98/08975, WO 98/4997 to Kristinsson and Janusson, Entitled Dual Durometer Silicon Liner for Prothesis, (Including Search Report), 20 pages.
EP 0 976 371 A1 Filed Jul. 30, 1998 to Philippe Garnier Entitled Fabrication Technique Involving Urethane (Including Search Report), 8 pages. and Abstract Translation of the Same.

* cited by examiner

*Primary Examiner*—Bruce E Snow
(74) *Attorney, Agent, or Firm*—Lackenbach Siegel, LLP; Andrew F. Young, Esq.

(57) ABSTRACT

The present invention relates to a supporting sleeve for a leg or arm stumps, namely a liner. The liner includes a sleeve made of an elastomeric and electrically insulating material that surrounds the stump starting from the distal end thereof. The sleeve has at least in part a surrounding layer made of a suitably conductive material.

11 Claims, 1 Drawing Sheet

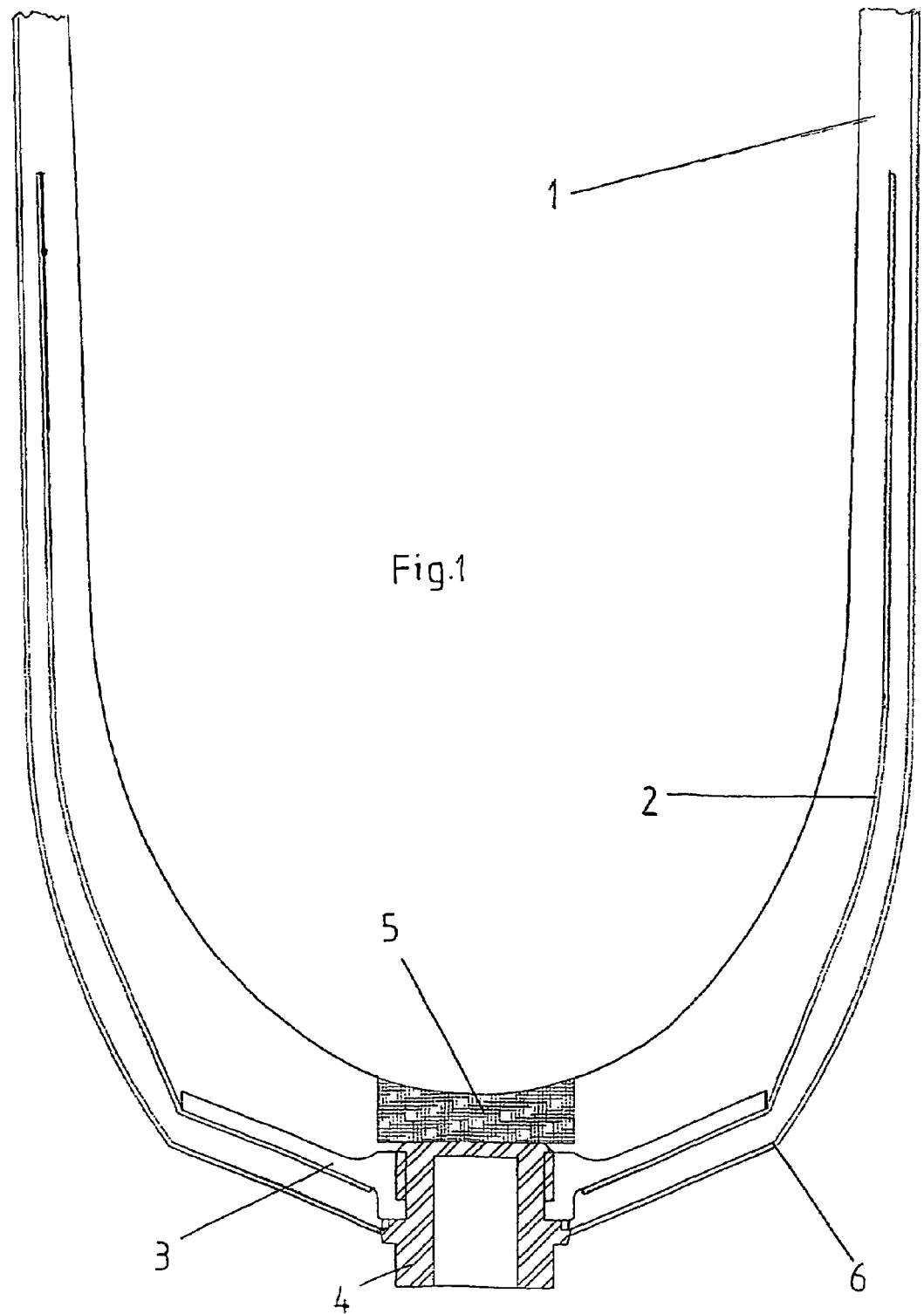

LINER

CROSS REFERENCE TO RELATED APPLICATIONS

This application claims priority from PCT/DE03/01835 filed Jun. 4, 2003, which in turn claims priority from DE 202 08 592.9 filed Jun. 4, 2002, the contents of each are incorporated herein by reference.

BACKGROUND OF THE INVENTION

1. Field of the Invention

The present invention relates to a supporting sleeve for leg or arm stumps, namely a liner. More specifically, the present invention relates to a liner for surrounding a stump from its distal end with an elastic electrically insulating material, wherein the sleeve has at least partially a layer of a conductive material.

2. Description of the Related Art

The related art involves liners for prostheses, such as leg prostheses, arm prostheses or the like, consisting of a sleeve enclosing the stump from its distal end and made of an elastic, electrically insulating material such as silicone, polyurethane. Such related art liners are shown, for example in WO 88/00032, WO 98/49977, and EP 0 976 371 A1.

Such liners are used as a cushioned connection between stump and prosthesis shaft, but are also used postoperatively in order to have a subsiding and shaping effect in the healing phase. A common post-surgical routine is to daily apply elastic bandages around the swollen amputation stump to counteract the swelling and accelerate the unavoidable muscle atrophy prior to using a liner. Unfortunately, stump bandaging, if incorrectly performed, may be ineffective and at worst injurious to the patient. After following initial amputation, and after a period using elastic bandages, the resulting stump is fitted to a liner.

Related liners or "sleeve shaped" articles for amputation stumps are known from WO 88/00032 to Klasson, and commonly provide a frusto-conical shape with a truncated end being rounded to receive the stump and a distal end being open to support the stump. As shown in Klasson, such liners often have a clasp or linking mechanism to join the liner to a prothesis and prevent unintended separation.

It is furthermore known that so-called phantom pain can arise after amputations, and can be positively influenced by electromagnetic screening of the stump, e.g. by an electrically conducting textile material applied in dry contact with the skin. An example of such related art is found in U.S. Pat. No. 4,653,473 to Batters.

As detailed in U.S. Pat. No. 4,653,473, a metal mesh in the form of a glove or sheet may be wrapped about a portion of the body and an electric current is applied at a shock pulse rate sufficient to "reduce pain . . . without causing heat build-up within the tissue of the human body." Such treatments are used to sooth arthritis, bone breaks, and other injuries.

However, what is not appreciated by the related art is the prior art is the need to combine the supportive aspects of a liner, with a capacity for every day use of electrotherapy while retaining the ready and secure connection to a prosthesis.

What is also not appreciated by the related art, is that postoperative treatment with elastic bandages may substantially diminished or eliminated and healing promoted by directly employing a liner having an adjustable and useable electrically conductive region for management of pain and discomfort while providing the same support found in elastic bandages.

Accordingly, there is a need for an improved liner allowing the ready use overcoming at least one of the detriments noted above.

OBJECTS AND SUMMARY OF THE INVENTION

An object of the present invention is to provide an embodiment that overcomes at least one of the detriments noted above.

Another object of the present invention is to a liner which has such an alleviating effect against stump pain, but without forfeiting the essential properties of a liner.

The present invention relates to a supporting sleeve for a leg or arm stumps, namely a liner. The liner includes a sleeve made of an elastomeric and electrically insulating material that surrounds the stump starting from the distal end thereof. The sleeve has at least in part a surrounding layer made of a suitably conductive material.

According to an embodiment of the present invention there is provided a supporting member for limb stumps, namely a liner, comprising: a sleeve member further comprising at least an elastomeric material, the elastomeric material being elastic and electrically insulating, the sleeve member defining a cavity for receiving a distal end of a stump, portions of the elastomeric material bounding the cavity for receiving the stump, the sleeve member further comprising a surrounding layer, and the surrounding layer composed of a conductive material.

According to another embodiment of the present invention there is provided a supporting sleeve for a stump, namely a liner, comprising: a sleeve member having a shape to bound at least a distal end of the stump, the sleeve member being at least partially an elastic and an electrically insulating material, and the sleeve member further comprises an electrically conductive layer bounding at least a portion of the stump.

According to another embodiment of the present invention there is provided a supporting sleeve for a stump, wherein: the electrically conductive layer is positioned externally to the sleeve member.

According to another embodiment of the present invention there is provided a supporting sleeve for a stump, wherein: the electrically conductive layer includes at least one of an electrically conductive elastomeric material, an electrically conductive textile material, an electrically conductive ceramic composite, and electrically conductive plastic material.

According to another embodiment of the present invention there is provided a supporting sleeve for a stump, wherein: the electrically conductive layer is a matrix of an electrically conductive material enclosed by an elastic material.

According to another embodiment of the present invention there is provided a supporting sleeve for a stump, wherein: the matrix is one of an ordered and a disordered assembly of thread members of an electrically conductive material.

According to another embodiment of the present invention there is provided a supporting sleeve for a stump, further comprising: means for forming a electrically conductive region between the stump and the electrically conductive layer.

According to another embodiment of the present invention there is provided a supporting sleeve for a stump, wherein: the means for forming a conductive region includes a liner cup member at a distal end of the liner.

According to another embodiment of the present invention there is provided a supporting sleeve for a stump, wherein: the conductive region is arranged proximate one of the distal end of the stump and a non-distal-end region of the stump within the liner.

According to another embodiment of the present invention there is provided a supporting sleeve for a stump, further comprising: a liner cup member at a distal end of the liner.

According to another embodiment of the present invention there is provided a supporting sleeve for a stump, wherein: the liner cup member is one of a cup member formed from an electrically conductive material and a cup member coated with an electrically conductive material, whereby the liner cup member According to another embodiment of the present invention there is provided a supporting sleeve for a stump, wherein: the liner cup member is in an electric communication with the electrically conductive layer.

According to another embodiment of the present invention there is provided a supporting sleeve for a stump, wherein: a measured electrical resistance between a surface of the stump installed in the liner and the conductive region is less than about $10^5$ ohms ($<10^5$ ohms).

According to another embodiment of the present invention there is provided a supporting sleeve for a stump, further comprising: means for enabling a secure connection between the supporting sleeve and an external prosthesis shaft member.

According to another embodiment of the present invention there is provided a supporting sleeve for a stump, further comprising: the means for enabling a secure connection being one of an electrically conducting means and an electrically insulating means.

According to another embodiment of the present invention there is provided a supporting sleeve for a stump, further comprising: means for forming an electrically conductive region between the stump and one of the electrically conductive layer and a liner cup electrically connected to the electrically conductive layer and positioned proximate the distal end of the stump.

According to another embodiment of the present invention there is provided a supporting sleeve for a stump, namely a liner, comprising: a sleeve member having a shape to bound at least a distal end of the stump, the sleeve member being at least partially an elastic and an electrically insulating material, the sleeve member further comprises an electrically conductive layer bounding at least a portion of the stump, the electrically conductive layer is not in direct contact with the distal end of the stump, and means for forming a electrically conductive region between the stump and the electrically conductive layer.

The above, and other objects, features and advantages of the present invention will become apparent from the following description read in conduction with the accompanying drawings, in which like reference numerals designate the same elements.

BRIEF DESCRIPTION OF THE DRAWINGS

FIG. 1 is a cross-sectional view of a liner according to one embodiment of the present invention.

DETAILED DESCRIPTION OF THE PREFERRED EMBODIMENTS

Reference will now be made in detail to several embodiments of the invention that are illustrated in the accompanying drawing and language. The drawings are in simplified form and are not to precise scale or shape. For purposes of convenience and clarity only, directional terms, such as top, bottom, up, down, over, above, and below may be used with respect to the drawings. These and similar directional terms should not be construed to limit the scope of the invention in any manner. Furthermore, the words "connect," "couple," and similar terms with their inflectional morphemes do not necessarily denote direct and immediate connections, but also include connections through mediate elements or devices.

Referring now to FIG. 1, a liner 1 having a distal and a proximate end is formed to include, in part, a preferably electrically conductive silicone material, and is shaped for receiving a leg or body stump. Liner 1 is provided with a cover 6 of a textile material. A layer 2 of an electrically conducting material, for example of metal threads or other metal or non-metal electrically conducting, is embedded in liner 1.

At the distal end of liner 1, there is located a pin adapter 4, known per se, for connecting to a lower leg prosthesis. During operation, liner 1 is supported from below by a supporting liner cup 3. In one preferred embodiment, pin adapter 4 and liner cup 3 consist of metal and are electrically conductive although other constructions are contemplated enabling the operation described herein.

Liner cup 3 is in contact with the incorporated matrix 2 of electrically conductive material.

For producing a therapeutically effective electrically conducting connection to the distal end of the stump, an electrically conductive region 5 is arranged above the pin adapter 4, and consists of, for example, a comfortable or felt-feel of an elastomeric material which is made electrically conductive by it's construction (for example it contains evaporated metal, containing conductive carbon, etc.) or has through threads of graphite, metal or the like contained therein or surrounding on a contact surface.

In a preferred construction, electrically conducting region 5 and liner 1 having substantially the same hardness of material whereby a stump inserted within the proximate end of liner 1 is received by surfaces having a similar therapeutic feel.

According to one alternative of the present invention, a supporting sleeve for leg or arm stumps, referred collectively to herein as a liner, consists of a sleeve surrounding the stump from its distal end, is of an elastic, electrically insulating material, characterized in that the sleeve has at least partially a layer 2 of conducting material running around it.

According to another embodiment of the invention, the electrically conducting layer 2 is applied to the sleeve on the outside and consists of a layer of an elastic, conductively equipped textile material or plastic. For example, electrically conducting layer 2 may optionally consist of a material onto which metal has been evaporated, adhered to, or otherwise applied enabling the conduction of electricity. Furthermore, for example, the plastic can be applied as an adhesive.

According to another embodiment of the invention, layer 2 is a textile mechanical reinforcement (formed as a matrix), beginning at the distal end of liner 2, of an electrically conductive material. As envisioned in this alternative embodiment, the matrix for example consists of an ordered or unordered threads, or a combination thereof, of a conductive material.

According to one particularly advantageous embodiment of the invention, a conductive region is arranged between the stump and the layer of conductive material 2, the conductive region preferably being arranged at least the distal end of the stump.

According to an alternative to the preferred embodiment of the invention, liner 2 has at its distal end a liner cup 3 providing support and if necessary a pin adapter 4 for connection to a prosthesis or other device. Here, liner cup 3 and optionally pin adapter 4 consist of an electrically conductive material, or being equipped with such effective to enable a therapeutic electromagnetic field proximate the distal end of liner 2.

Liner cup 3 and/or pin adapter 4 are in electrically connection with layer 2 of electrically conductive material, the conductive region being arranged between the stump and the liner cup 3 and/or the pin adapter 4.

It is recognized herein, that if liner 1 is used exclusively for non-weight-bearing postoperative treatment only, the liner cup 3 and pin adapter 4 may be omitted.

In another alternative embodiment of the present invention, an electrical resistance of $<10^5$ ohm (less than about $10^5$ ohms) is preferably present or maintained between the stump and the conductive region thereby achieving one of the needs noted above.

In the claims, means-or step-plus-function clauses are intended to cover the structures described or suggested herein as performing the recited function and not only structural equivalents but also equivalent structures. Thus, for example, although a nail, a screw, and a bolt may not be structural equivalents in that a nail relies on friction between a wooden part and a cylindrical surface, a screw's helical surface positively engages the wooden part, and a bolt's head and nut compress opposite sides of a wooden part, in the environment of fastening wooden parts, a nail, a screw, and a bolt may be readily understood by those skilled in the art as equivalent structures.

Having described at least one of the preferred embodiments of the present invention with reference to the accompanying drawings, it is to be understood that the invention is not limited to those precise embodiments, and that various changes, modifications, and adaptations may be effected therein by one skilled in the art without departing from the scope or spirit of the invention as defined in the appended claims.

The invention claimed is:

1. A supporting sleeve for a body stump, said supporting sleeve having at least a distal end and an open receiving end, namely a liner, comprising:
    a sleeve member having an inner surface defining a concave shape proximate said distal end for bounding at least a portion of said body stump during a use thereof;
    said sleeve member being at least partially an elastic and an electrically insulating material along said inner surface;
    said sleeve member further comprises a first portion electrically conductive layer proximate said distal end and a second portion electrically conductive layer being spaced from said inner surface by at least a portion of said elastic and electrically insulating material of said sleeve member along said open receiving end; and
    means for forming a electrically conductive region between said first and second portions of and said electrically conductive layer including a liner cup member at said distal end of said sleeve member.

2. A supporting sleeve for a body stump, according to claim 1, wherein:
    said liner cup member is one of a cup member formed from an electrically conductive material and a cup member coated with an electrically conductive material, whereby said liner cup member is in an electric communication with said electrically conductive layer.

3. A supporting sleeve for a body stump, according to claim 1, wherein:
    a measured electrical resistance between said surface and said conductive region is less than about $10^5$ ohms.

4. A supportive sleeve for a body stump, according to claim 1, further comprising:
    means for enabling a secure connection between said supporting sleeve and an external prosthesis shaft member.

5. A supporting sleeve for a body stump, according to claim 4, further comprising:
    said means for enabling a secure connection being one of an electrically conducting means and an electrically insulating means.

6. A supporting sleeve for a body stump, according to claim 1, wherein:
    said electrically conductive layer includes at least one of an electrically conductive elastomeric material, an electrically conductive textile material, electrically conductive threads of graphite, an electrically conductive metallic material, and electrically conductive plastic material.

7. A supporting sleeve for a body stump, according to claim 1, wherein:
    said electrically conductive layer is a matrix of an electrically conductive material enclosed by an elastic material.

8. A supportive member, configured to conform to an external stump comprising:
    a supportive concave sleeve having an inner surface defining a receiving concave shape having an inner distal end and an opposing outer open non-distal end;
    said supportive concave sleeve being an elastic electrically insulating material;
    a partially rigid liner member in said supportive concave sleeve having a first portion and a second portion;
    said first portion of said liner member being electrically conductive and being on said inner surface of said concave sleeve at said distal end thereof opposite said non-distal end;
    a second portion of said liner member having a concave shape and being electrically conductive and extending away from said first portion within an inner portion of said supportive concave sleeve, whereby said second portion is electrically conductive with said first portion but is spaced from said inner surface of said elastic insulating material of said sleeve and electrically separated there from;
    said first portion and said second portion of said liner member being an electrically conductive layer;
    said electrically conductive layer constructed from at least one of an electrically conductive elastomeric material, an electrically conductive textile material, an electrically conductive fiber material, an electrically conductive metallic material, and an electrically conductive plastic material; and
    an electrically conductive cup member in said electrically conductive layer proximate said first portion thereof.

9. A supportive member, according to claim 8, wherein:
    said electrically conductive layer includes a matrix of an electrically conductive material enclosed by an elastic material.

10. A supportive member, according to claim 9, wherein:
    said matrix is at least one of an ordered and a disordered assembly of thread members of an electrically conductive material.

11. A supportive member, according to claim 8, further comprising:
    means for enabling an electrical connection between said conductive cup member and an external prosthesis member.

* * * * *